United States Patent
Sathaye et al.

(10) Patent No.: US 8,271,087 B2
(45) Date of Patent: Sep. 18, 2012

(54) METHODS AND SYSTEMS FOR SELECTING CAPTURE VERIFICATION MODES

(75) Inventors: Alok Sathaye, Boston, MA (US); Scott A. Meyer, Lakeville, MN (US); Derek D. Bohn, Woodbury, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 313 days.

(21) Appl. No.: 12/697,853

(22) Filed: Feb. 1, 2010

(65) Prior Publication Data

US 2010/0131027 A1    May 27, 2010

Related U.S. Application Data

(63) Continuation of application No. 11/168,276, filed on Jun. 28, 2005, now Pat. No. 7,657,314.

(51) Int. Cl.
*A61N 1/08* (2006.01)

(52) U.S. Cl. .............. 607/28; 607/27; 607/30; 600/509; 600/513; 600/522

(58) Field of Classification Search ............ 607/27, 607/28, 30; 600/509, 513, 522
See application file for complete search history.

(56) References Cited

U.S. PATENT DOCUMENTS

| | | | |
|---|---|---|---|
| 4,969,467 A | 11/1990 | Callaghan et al. | |
| 5,350,410 A | 9/1994 | Kleks et al. | |
| 6,128,535 A | 10/2000 | Maarse | |
| 6,285,908 B1 | 9/2001 | Mann et al. | |
| 6,295,471 B1 | 9/2001 | Bornzin et al. | |
| 6,473,649 B1 | 10/2002 | Gryzwa et al. | |
| 6,643,549 B1 | 11/2003 | Bradley et al. | |
| 6,766,197 B1 | 7/2004 | Levine | |
| 6,788,971 B1 | 9/2004 | Sloman et al. | |
| 6,819,955 B2 | 11/2004 | Levine | |
| 2002/0078968 A1 | 6/2002 | Spinelli et al. | |
| 2003/0069611 A1* | 4/2003 | Levine | 607/27 |
| 2003/0083710 A1 | 5/2003 | Ternes et al. | |
| 2003/0083711 A1 | 5/2003 | Yonce et al. | |
| 2005/0137640 A1* | 6/2005 | Freeberg et al. | 607/28 |

OTHER PUBLICATIONS

U.S. Office Action dated Apr. 3, 2008 for U.S. Appl. No. 11/168,276, 11 pages.
U.S. Office Action dated Nov. 5, 2008 for U.S. Appl. No. 11/168,276, 12 pages.
U.S. Office Action dated Mar. 10, 2009 for U.S. Appl. No. 11/168,276, 10 pages.
Notice of Allowance dated Sep. 24, 2009 from U.S. Appl. No. 11/168,276, 4 pages.
Office Action Response dated May 18, 2009 from U.S. Appl. No. 11/168,276, 10 pages.

(Continued)

*Primary Examiner* — Carl H Layno
*Assistant Examiner* — Natasha Patel
(74) *Attorney, Agent, or Firm* — Seager, Tufte & Wickhem, LLC (57) ABSTRACT

Methods and systems are directed to selecting from a variety of capture verification modes. A plurality of capture verification modes, including a beat by beat capture detection mode and a capture threshold testing mode without intervening beat by beat capture detection is provided. An efficacy of at least one of the capture verification modes is evaluated and, based on the evaluation, a capture verification mode is selected.

16 Claims, 7 Drawing Sheets

OTHER PUBLICATIONS

Interview Summary dated Apr. 27, 2009 from U.S. Appl. No. 11/168,276, 2 pages.
Office Action Response dated Feb. 3, 2009 from U.S. Appl. No. 11/168,276, 11 pages.
Interview Summary dated Jan. 30, 2009 from U.S. Appl. No. 11/168,276, 2 pages.
Office Action Response dated Jul. 7, 2008 from U.S. Appl. No. 11/168,276, 16 pages.

* cited by examiner

METHODS AND SYSTEMS FOR SELECTING CAPTURE VERIFICATION MODES

RELATED PATENT DOCUMENTS

This application is a continuation of U.S. patent application Ser. No. 11/168,276 filed on Jun. 28, 2005, now U.S. Pat. No. 7,657,314 which is incorporated herein by reference in its entirety.

FIELD OF THE INVENTION

The present invention relates generally to capture verification, and more particularly to selecting between capture verification modes used in connection with cardiac pacing.

BACKGROUND OF THE INVENTION

When functioning normally, the heart produces rhythmic contractions and is capable of pumping blood throughout the body. However, due to disease or injury, the heart rhythm may become irregular resulting in diminished pumping efficiency. Arrhythmia is a general term used to describe heart rhythm irregularities arising from a variety of physical conditions and disease processes. Cardiac rhythm management systems, such as implantable pacemakers and cardiac defibrillators, have been used as an effective treatment for patients with serious arrhythmias. These systems typically comprise circuitry to sense electrical signals from the heart and a pulse generator for delivering electrical stimulation pulses to the heart. Leads extending into the patient's heart are connected to electrodes that contact the myocardium for sensing the heart's electrical signals and for delivering stimulation pulses to the heart in accordance with various therapies for treating the arrhythmias.

Cardiac rhythm management systems including pacemakers operate to stimulate the heart tissue adjacent to the electrodes to produce a contraction of the tissue. Pacemakers are cardiac rhythm management systems that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

When a pace pulse produces a contraction in the heart tissue, the electrical cardiac signal preceding the contraction is denoted the captured response (CR). The captured response typically includes an electrical signal, denoted the evoked response signal, associated with the heart contraction, along with a superimposed artifact signal associated with residual post pace polarization at the electrode-tissue interface. The magnitude of the residual post pace polarization signal, or pacing artifact, may be affected by a variety of factors including lead polarization, after-potential from the pace pulse, lead impedance, patient impedance, pace pulse width, and pace pulse amplitude, for example.

A pace pulse must exceed a minimum energy value, or capture threshold, to produce a contraction. It is desirable for a pace pulse to have sufficient energy to stimulate capture of the heart without expending energy significantly in excess of the capture threshold. Thus, accurate determination of the capture threshold is required for efficient pace energy management. If the pace pulse energy is too low, the pace pulses may not reliably produce a contractile response in the heart and may result in ineffective pacing.

If the pacemaker delivers pacing pulses having an energy that significantly exceed the capture threshold, the patient may experience discomfort and the battery life of the device will be shorter. Determining the capture threshold of the heart allows adjustment of the pacing energy to a level that reliably produces capture without unnecessary energy expenditure.

SUMMARY OF THE INVENTION

The present invention is directed to a method and system for selecting capture verification modes. In accordance with one embodiment, a cardiac therapy method includes selection of capture verification modes. The method requires providing a plurality of capture verification modes, where at least a first capture verification mode includes an automatic beat-by-beat capture detection, and a second capture verification mode includes capture threshold testing without intervening beat by beat capture detection. The efficacy of at least one of the provided capture verification modes is evaluated and, based on the evaluation, a capture verification mode is selected.

In a further embodiment of the invention, a cardiac rhythm management system may be configured to implement a variety of capture verification modes. The cardiac rhythm management system includes electrodes capable of electrically coupling to a heart, a pulse generator coupled to the electrodes for delivering pacing pulses to the heart, circuitry for implementing a plurality of capture verification modes, and a processor for evaluating and selecting the capture verification modes. Circuitry for implementing capture verification modes includes automatic capture detection (ACD) circuitry for implementing a beat by beat automatic capture detection mode, and capture threshold testing (CTT) circuitry for implementing a capture threshold testing mode without intervening capture detection.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings that form a part hereof, and in which is shown by way of illustration, various embodiments in which the invention may be practiced. It is to be understood that other embodiments may be utilized and structural and functional changes may be made without departing from the scope of the present invention.

After delivery of a pacing pulse to a heart chamber, various cardiac responses to the pacing pulse are possible. For example, the pacing pulse may generate a propagating wavefront of depolarization resulting in a contraction of the heart chamber. In such an instance, the pacing pulse is said to have captured the heart chamber. Capture of the heart chamber may occur if the pacing pulse has sufficient energy to initiate the depolarization wavefront and is delivered during a period of time that the cardiac tissue is non-refractory. If the pacing pulse does not produce contraction of the cardiac tissue, the cardiac response is referred to as non-capture. It is desirable for a pace pulse to have sufficient energy above the capture threshold to capture the heart without expending excess energy above the capture threshold.

Whether an applied electrical pacing stimulus captured the heart may be determined by evaluating the post-pace electrical signal produced by the heart. The process of evaluating the heart's electrical signals may be performed automatically, for example, using systems having patient-implantable and/or patient-external circuitry and/or components.

In one implementation, an implantable cardiac rhythm management (CRM) device, such as a pacemaker or other implantable device, may be used to automatically evaluate the electrogram signals produced by the heart to determine the cardiac response to a pacing pulse. For example, an implantable cardiac rhythm management device may determine the cardiac response to a pacing pulse using electrogram signals on a beat to beat basis.

In another implementation, the cardiac response to pacing may be evaluated using a patient-external computing system such as an advanced patient management (APM) system. Advanced patient management systems may involve one or more distinct medical devices that are accessible through various communications technologies. Patient and/or device information may be acquired by the one or more medical devices and downloaded periodically or on command to a patient information server. The physician and/or the patient may communicate with the medical devices and/or the patient information server, for example, to access patient data, to modify device parameters, and/or to initiate, terminate or adjust processes, e.g., therapy and/or diagnostic processes, performed by the medical devices or the patient information server.

Embodiments of the invention are directed to methods and systems for selecting a cardiac verification mode used for determining the capture threshold of one or more cardiac chambers, e.g., atrial and/or ventricular chambers. The capture threshold is defined as the lowest pacing energy that consistently captures the heart. A capture threshold determined by the selected capture verification mode is used to adjust the pacing energy delivered to the patient so that pacing is provided at an energy level that reliably produces capture without unnecessary energy expenditure. In various embodiments described herein, selecting the capture verification mode involves selecting between independent capture verification modes, such as an automatic beat-to-beat capture detection (ACD) mode, a capture threshold testing (CTT) mode, a trend only mode with a physician programmed output with daily measurement, or no capture verification. In further embodiments, selection of a capture verification mode may be based on a physician selected or pre-determined hierarchy.

The automatic capture detection (ACD) mode may be used, for example, to monitor capture results in one or more of a left atrium, right atrium, left ventricle, and right ventricle on a beat-by-beat basis. In one example, the ACD process may involve adjusting the pacing threshold after detecting loss of capture. For example, if loss of capture is detected by the ACD process, the pacing energy may be ramped up over one or more beats until capture is detected.

In another example, if loss of capture is detected by the ACD process, a threshold search is triggered. The threshold search involves delivering pacing pulses at variable energy levels to determine the capture threshold. The capture threshold determined by the threshold search is used to set the pacing energy. Automatic capture detection (ACD) mode may additionally involve controlling back up pacing when a pace pulse delivered to the heart fails to produce a captured response. A back up pace may be delivered, for example, about 70-80 ms after the initial pace pulse.

A patient's capture threshold may fluctuate significantly during the first weeks after implantation. Soon after implantation, the capture threshold typically increases to a peak value and then gradually decreases. Eventually, the capture threshold becomes relatively stable at a level higher than the initial implantation threshold but less than the peak value. Various physiological factors may cause fluctuations in the capture threshold level after implantation, including, for example, illness, changes in the lead/tissue interface, or use of medication.

The use of ACD mode allows the capture threshold to be adjusted frequently to correspond to variations in the capture threshold of the patient. In some implementations, the pacing energy may be adjusted after every beat. In other implementations, the pacing energy may be adjusted after a threshold search is performed following a detected loss of capture. When operating in ACD mode, the frequency of threshold searches may be limited to a predetermined frequency. For example, in one scenario, threshold searches are performed about once per hour and pacing energy adjustment may occur after each threshold search.

The frequency of pacing energy adjustment allows ACD mode to closely track variations in the patient's capture threshold. When operating effectively, ACD mode provides consistent pacing using a pacing energy just above the capture threshold, for example, 0.2-0.5 volts above the capture threshold. Setting the pacing energy slightly above the capture threshold provides a safety margin to ensure consistent pacing. The ability to closely match the pacing energy to the capture threshold using a smaller safety margin advantageously provides an increased battery life.

However, in some situations, reliable beat by beat capture detection required for effective operation of ACD mode may be difficult to obtain or maintain. Unreliable capture detection may be caused, for example, by a high occurrence of intrinsic or fusion beats, by changes in physiologic conditions, by device programming incompatible with capture detection, by system noise, or by other factors. In these situations, operating in ACD mode may cause more frequent backup pacing and more frequent threshold searches. After loss of capture is detected in ACD mode, the device may operate in a high energy pacing default mode until a threshold search is performed. Thus, when ACD mode is ineffective, the battery longevity savings associated with pacing at a lower safety margin may not be realized.

Another capture verification mode that may be selected involves performing a sequence of threshold searches that occur according to a time schedule. Capture threshold testing (CTT) mode may be used to determine the capture threshold in any or all of the left atrium, right atrium, left ventricle, and right ventricle. In CTT mode, a threshold search may be performed according to a regular periodic time schedule, e.g., once per day, once every 21 hours, performed according to a random time schedule, or performed according to some other schedule. The pacing energy is adjusted based on the capture threshold determined by one or more of the most recent capture threshold measurements. In one implementation, a capture threshold test may be automatically initiated by the pacemaker or by the APM system according to a predetermined time schedule, for example. In another implementation, the APM system may request a series of tests leading up to a scheduled device follow-up visit (in-office or remote). In yet another implementation, a threshold search may be initiated by a command to the pacemaker from a physician or other person.

The threshold search comprises delivering a sequence of pacing pulses to a heart chamber and determining if the pacing pulses capture the heart chamber. The energy of the pacing pulses delivered by the threshold search may be decreased in discrete steps until a predetermined number of loss-of-capture events occur. Upon detection of loss of capture, the stimulation energy may be increased in discrete steps until a predetermined number of capture events occur to confirm the capture threshold. Other procedures for implementing capture threshold searching may be utilized. In one example, the pacing energy may be increased in discrete steps until capture is detected. In another example, the pacing energy may be adjusted according to a binomial search pattern.

In some scenarios, the threshold searches are ineffective and an accurate capture threshold cannot be obtained. If CTT mode is unable to provide an accurate capture threshold, the system may revert to a default mode that involves pacing at a relatively high voltage without capture verification. The pacing energy used for the default mode involves a large margin of safety making this operation in the default mode more energy consumptive than either ACD mode or CTT mode. Alternatively, the system may transition to a physician programmed output that includes a daily threshold measurement, known as a trend only mode.

Figure 1:
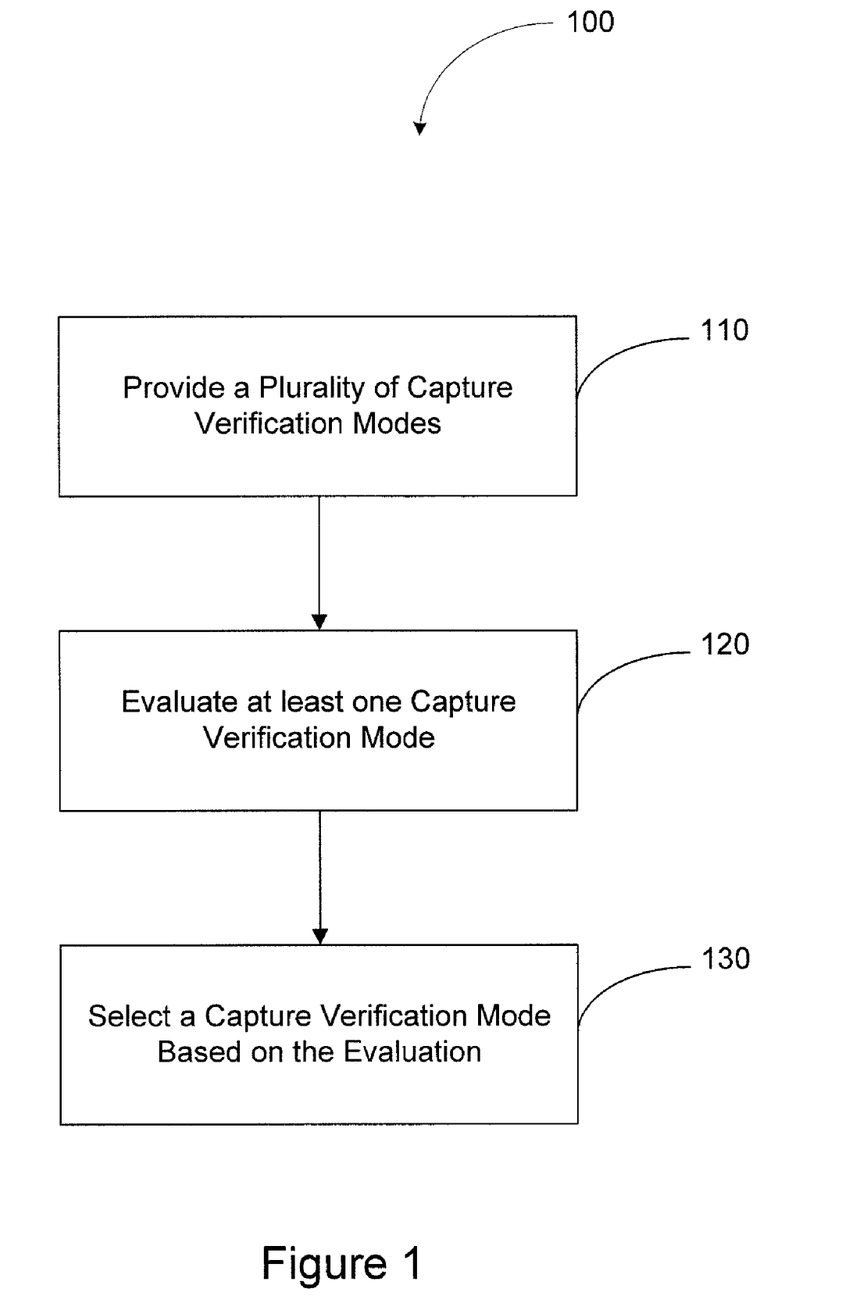
FIG. 1 illustrates a flowchart of a method for selecting capture verification modes in accordance with embodiments of the invention.

FIG. 1 is a flowchart illustrating a cardiac therapy method involving selection of a capture verification mode in accordance with embodiments of the invention. A plurality of capture verification modes is provided 110. As previously discussed, the plurality of modes may include an automatic capture detection (ACD) mode comprising beat to beat capture detection and a (CTT) mode comprising a sequence of periodically performed threshold searches.

At least one of the plurality of capture verification modes is evaluated 120 with respect to efficacy in delivering an appropriate level of capture verification benefit to the patient. For example, an efficacy measure may include a performance metric. A capture verification mode, e.g., ACD mode or CTT mode, may be selected 130 based on the evaluation. In addition, in some embodiments, the selected mode may be a fixed voltage mode or a trend only mode. The selected capture verification mode is used to monitor the capture threshold of the patient.

In accordance with some embodiments, evaluating the efficacy of a capture verification mode and selecting one of the plurality of capture verification modes may be performed automatically by implantable CRM devices or by advanced patient management (APM) systems. According to some embodiments, assessing the efficacy and selecting the capture verification mode may be performed manually. In one implementation, data related to capture verification mode efficacy may be acquired by a pacemaker and transferred to an APM server. A physician or other person may review the collected data, select a capture verification mode based on the collected data, and communicate with the pacemaker via the APM server to select an appropriate capture verification mode.

Figure 2:
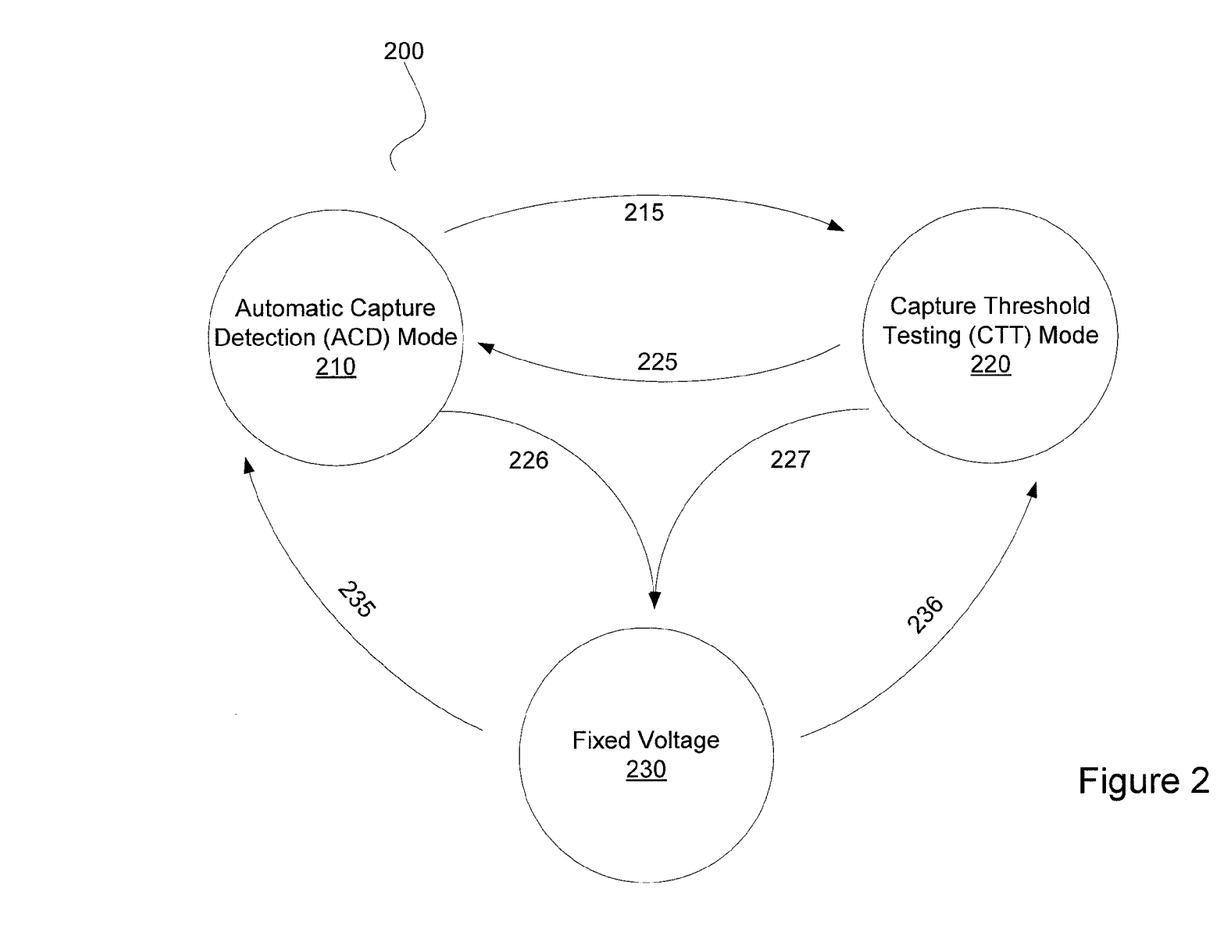
FIGS. 2 and 3 are state diagrams illustrating capture verification mode selection in accordance with embodiments of the invention.

FIG. 2 is a state diagram 200 illustrating various processes involved in selecting a capture verification mode in accordance with embodiments of the invention. Transitions into or out of the modes 210, 220, 230 illustrated in diagram 200 may be implemented manually by a physician or may be implemented by a device that is programmed to perform the selection process automatically or on command. Transitioning between capture verification modes 210, 220, and 230 allows the capture verification mode to be modified based on dynamically changing patient conditions. The capability to select between capture verification modes provides device operation that increases battery longevity without a compromising patient safety.

For purposes of describing the capture verification mode selection process, it is assumed that the device initially operates in ACD mode 210. While operating in ACD mode 210, pacing pulses are delivered at a pacing energy that is a relatively small margin, e.g., about 0.5 V, above the capture threshold. After each pace, the system determines if the pacing pulse captured the heart tissue. For each non-captured beat, the device may deliver a back-up pace. The energy of the back up pace is sufficiently high to ensure capture. In some implementations, the back up pace is delivered at a maximum energy level, e.g., 5 V.

If loss of capture is detected, or of other factors are detected that may disrupt capture detection, a threshold search is performed. If a capture threshold cannot be determined by the threshold search, or if loss of capture persists as determined by beat to beat capture detection, the device may revert 226 to a fixed voltage mode 230 without capture verification. Periodically, while pacing in the fixed voltage mode 230, a threshold search may be conducted. If a capture threshold is acquired by the threshold search, then the device may transition 235 to operate in ACD mode 210. If a capture threshold is not acquired by the threshold search, then the device remains in the fixed voltage mode 230.

While operating in ACD mode 210, the efficacy of the ACD mode 210 is assessed. Under some conditions, while operating in ACD mode 210, the benefits of ACD mode may not be realized. For example, the benefits of ACD mode may not accrue if one or more of the following factors is present: the frequency of backup pacing is high, the retry rate of threshold searches is high, atrial fibrillation is detected, the AV-delay programming is incompatible with ACD mode, an elevated capture threshold is present, low percentage of ventricular paces, and/or other conditions affecting the efficacy of ACD mode. These factors may be periodically evaluated. If the evaluation indicates that the benefits of ACD mode are not being realized, and/or that operation in CTT mode 220 is likely to enhance patient safety as compared to an ACD mode 210, CCT mode 220 may be selected which triggers a transition 215 into CTT mode 220.

In CTT mode 220, threshold searches are performed periodically, e.g., every 21 hours or according to another time schedule. If a threshold search is successful, the pacing energy is adjusted based on one or more most recent threshold searches. For example, the pacing energy may be adjusted to about twice the most recent capture threshold or to about 2 volts, whichever is higher. The pacing safety margin used while operating in CTT mode may be greater than the safety margin used for ACD mode. An increased pacing safety margin is necessary because beat to beat automatic capture detection is not used in CTT mode. Thus to ensure continuous therapeutic pacing support to the patient, the pacing threshold must be high enough to provide consistent pacing between threshold searches, e.g., about 21 hours.

If one or more threshold searches are unsuccessful, the device may revert to 227 to the fixed voltage mode 230 without capture verification. Periodically, a threshold search may be conducted while in fixed voltage mode 230. If a capture threshold is acquired by the threshold search, then the device may begin 236 operating in CTT mode 220. If a capture threshold is not acquired by the threshold search, then the device remains in the fixed voltage mode 230.

The efficacy of operating in CCT mode 220 is assessed. If it is likely that benefits associated with ACD mode 210, such as battery longevity, improved patient safety, and/or other benefits, are likely to be realized in ACD mode 210, then ACD mode 210 may be selected and the device transitions 225 into ACD mode. The factors used to evaluate the likelihood that the benefits of ACD mode 210 will be accrued may comprise, for example, the absence of fusion beats detected during threshold searches, high signal to noise ratio on the channel used for capture detection, AV-delay programming compatible with ACD mode, results of AV search or Reverse mode switch algorithms, history of atrial tachycardia mode switch response, or relatively low capture threshold, among other factors.

In some embodiments, the device may store information associated with capture verification mode transitions for further evaluation. The stored information may be transmitted to a separate computing device, such as an APM system, for further evaluation or trending.

Figure 3:
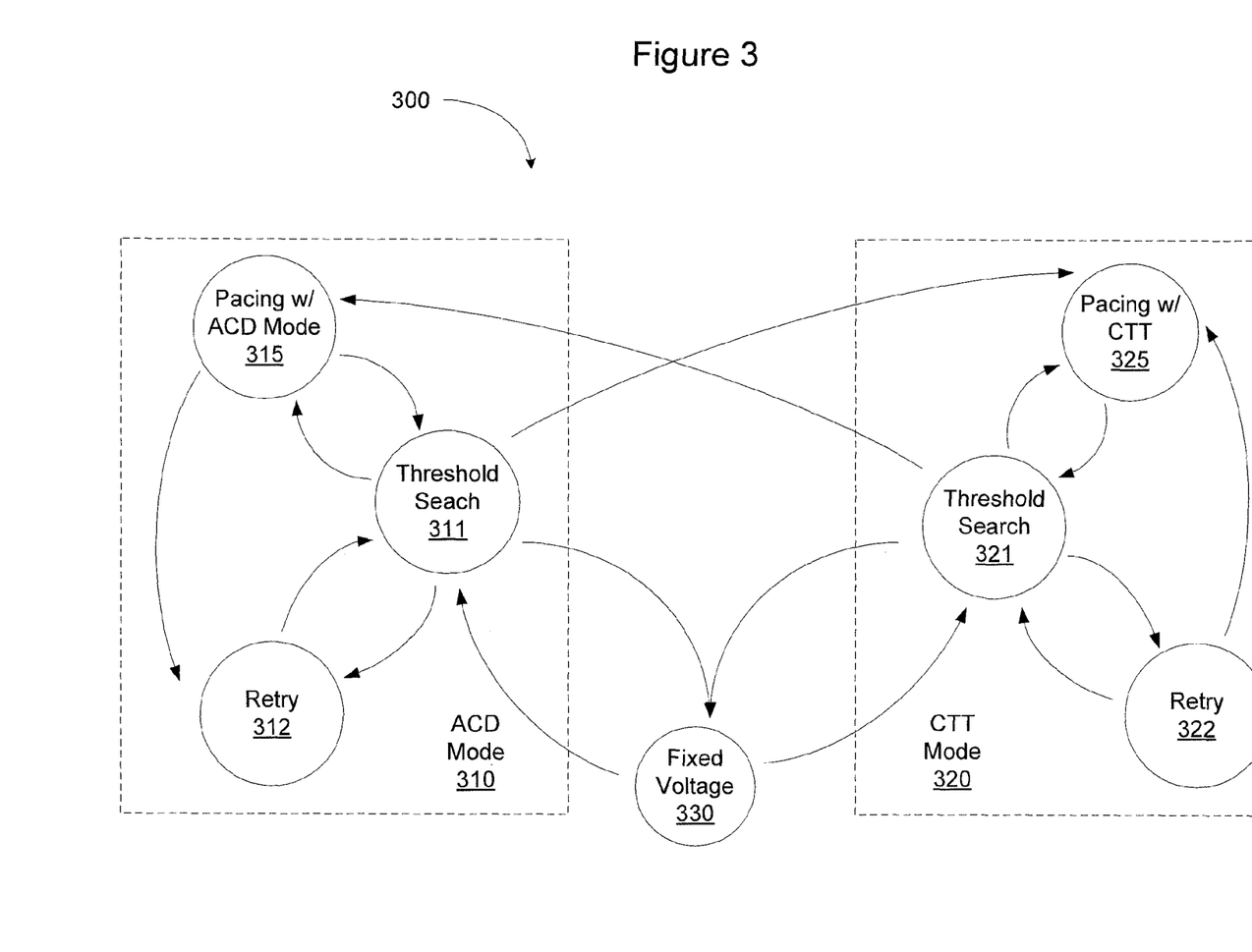

FIG. 3 illustrates state diagram illustrating a capture verification mode selection process in accordance with embodiments of the invention. According to this embodiment, pacing may be delivered to a patient in ACD mode 310, CTT mode 320, or fixed voltage mode 330. To facilitate the discussion, it is assumed that the device is initially operating in ACD mode 310. Pacing is delivered to the patient at a pacing voltage above the capture threshold, for example the capture threshold plus about 0.5 volts. Beat by beat, the device senses for an evoked response and determines 315 if the cardiac pacing response is a captured response or a non-captured response.

Periodically, e.g., about every 21 hours, or if the device detects certain conditions, e.g., loss of capture, noise on the channel used to detect capture, and low capture threshold, e.g., less than about 2 mV, signal to artifact (SAR) ratio of less than about 2, the device may perform a threshold search 311 to determine the capture threshold. If any of the conditions listed above are detected, but a threshold search was previously performed within a predetermined period, for example about 1 hour, the device may enter a retry state 312 wherein the device waits for a period of time, for example, until about an hour has passed since the previous threshold search. The device performs one or more threshold searches 311 to attempt to determine the capture threshold. For example, the device may perform a sequence of threshold searches 311 such as one threshold search performed per hour. If a threshold search is successful, the device resumes beat to beat capture detection 315.

However, if the threshold searches 311 are unsuccessful, or are successful but indicate a capture threshold lower than a predetermined threshold for safe pacing, transition to a fixed voltage mode 330 may occur. When operating in the fixed voltage mode 330, the system paces at a high output pace energy, for example, about twice the capture threshold or about 3.5 volts, whichever is higher. The system continues to attempt to acquire a capture threshold by periodically performing threshold searches 311. In one implementation, for example, while in the fixed voltage mode 330, threshold searches 311 may be performed about once every week.

The efficacy of the ACD mode 310 is evaluated. The efficacy evaluation of the ACD mode 310 may involve determining if the benefits of ACD mode 310 are realized while the device is operating in ACD mode 310. For example, frequent backup pacing, frequent threshold searches, frequent reversion to or extended time in fixed voltage mode pacing are factors indicating the benefits of ACD mode are possibly not realized. Frequent high energy pacing negates any gain to battery longevity while in ACD mode and may be equivalent to setting a fixed pacing amplitude.

According to one embodiment, a transition from ACD mode 310 to CTT mode 320 may occur under one or more of the following conditions: 1) the frequency of threshold searches exceeds a predetermined threshold, 2) the frequency of back up paces delivered exceeds a predetermined threshold; 3) the time spent in fixed voltage mode 330 and/or in the retry state 312 exceeds a predetermined threshold. If any one or more of these conditions meet the respective threshold criteria, or if other conditions are present that indicate ACD mode is ineffective, CTT mode 325 may be selected.

The efficacy evaluation may be performed manually or automatically. In one implementation, the efficacy evaluation occurs according to a predetermined time schedule. If the efficacy evaluation indicates that ACD mode 310 is not effective and the capture verification mode should be changed, then CTT mode 320 may be selected.

In another implementation, the efficacy evaluation is updated continuously by the device each time a significant event occurs, e.g., a threshold search is performed, back up pace delivered, or the device remains in retry or fixed voltage mode.

When operating in the CTT mode 320, the device delivers 325 pacing pulses at a pacing energy that is greater than the pacing energy used in ACD mode 310. For example, the pacing energy may be set to the greater of either about two times a previously determined capture threshold or about 2 volts. Beat to beat capture detection is not performed after delivery of the pacing pulses.

In one implementation, while operating in CTT mode 325, threshold searches 321 are performed once every 21 hours, however, other random or regular time schedules may be used to schedule the threshold searches. If the threshold search 321 is successful then the device continues 325 to deliver pacing without beat to beat capture detection and with periodic threshold searches 321 to set the pacing energy.

If a threshold search 321 fails, the system transitions into a retry state 322. While in the retry state 322, the pacing energy is based, for example, on one or more of the previously successful capture thresholds acquired. When it is time for a threshold search to be performed, the device transitions from the retry state 322 and the threshold search 321 is performed.

For example, after one hour in retry mode 322, a threshold search 321 may be conducted. If the threshold search 321 is successful, then the device may resume pacing 325 in CTT mode 320.

If a predetermined number, for example about 3, threshold searches 321 yield unsuccessful capture threshold results, or if the threshold search results are lower than a minimum threshold, a transition to fixed voltage pacing mode 330 may occur.

The efficacy of the capture verification mode may be periodically evaluated to determine whether re-entry into ACD mode 310 from CTT mode 320 is desirable. For example, the various factors may be evaluated to determine the likelihood of beneficial operation in ACD mode 310. In one implementation, if battery life would likely be increased by operation in ACD mode 310, then ACD mode 310 is selected and the device transitions from CTT mode 320 operation to ACD mode 310 operation.

Figure 4:
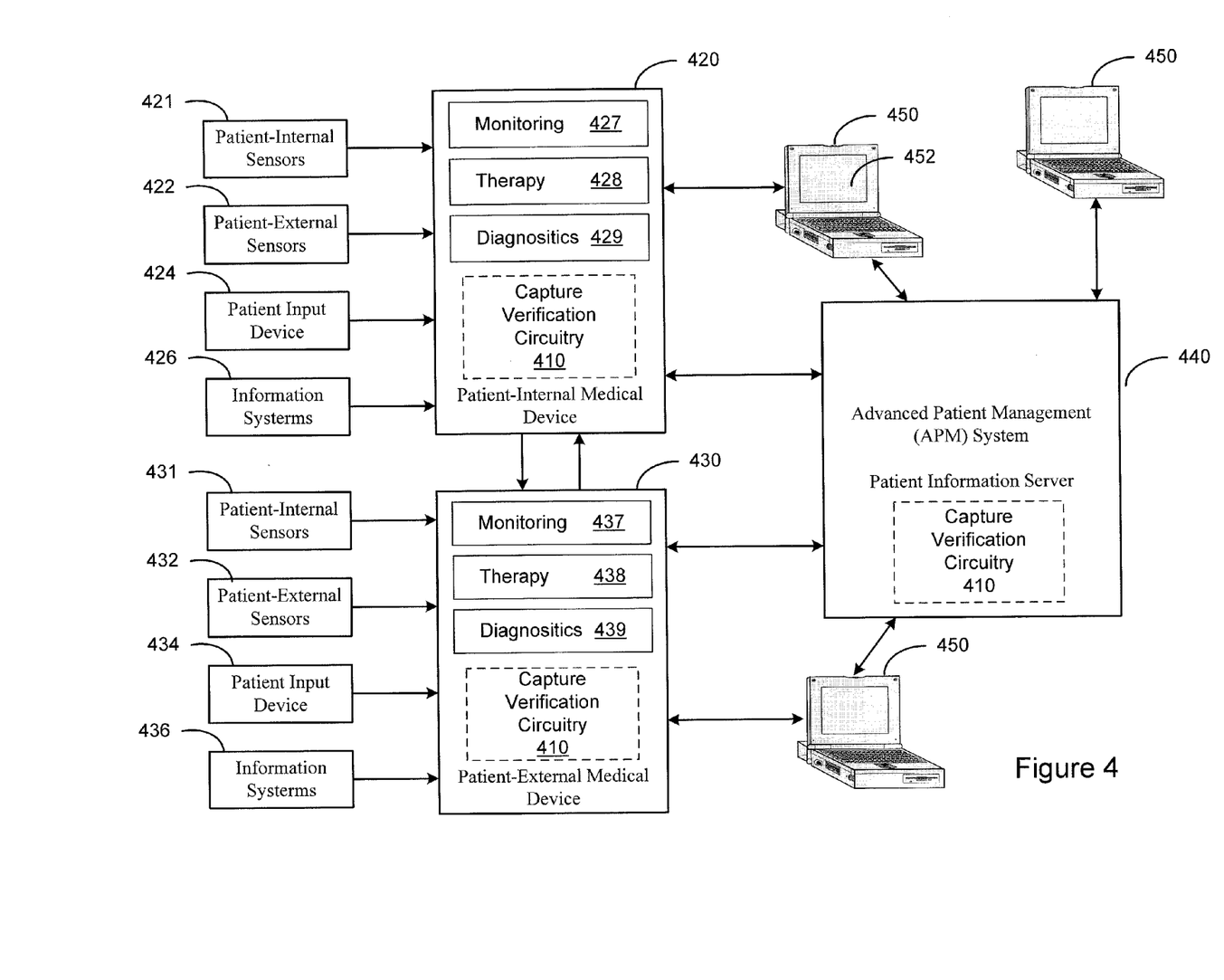
FIG. 4 is a block diagram of a system that may be used to implement capture verification mode selection in accordance with embodiments of the invention.

FIG. 4 is a block diagram of a medical system that may be used in conjunction with an advanced patient management (APM) system to implement a capture verification mode selection process in accordance with embodiments of the invention. The medical system may include, for example, one or more patient-internal medical devices 420 and one or more patient-external medical devices 430. Each of the patient-internal 420 and patient-external 430 medical devices may include one or more of a patient monitoring unit 427, 437, a diagnostics unit 429, 439, and/or a therapy unit 428, 438. Capture verification circuitry 410, in accordance with embodiments of the invention, may include circuitry implementing various capture verification modes, circuitry for assessing the efficacy of capture verification modes, a controller for selecting one or none of the capture verification modes, a timing circuit, and a memory, for example. Components of the capture verification circuitry 410, may be housed in a patient internal medical device 420, a patient external medical device 430, and a remote network server system such as advanced patient medical (APM) system 440 or in any combination of the above-mentioned devices 420, 430, 440.

Selection of the capture verification modes in accordance with various embodiments of the invention may be performed automatically by the capture verification circuitry or manually by a physician or other person using information provided by the medical system. In one implementation, the internal device 420 may comprise a pacemaker that comprises all components of the capture verification circuitry. The pacemaker evaluates the efficacy of a capture verification mode selects a capture verification mode based on the efficacy evaluation.

In another implementation, the pacemaker comprises circuitry for implementing ACD mode and CTT mode. The pacemaker communicates with an APM server that houses the selection processor. Based on data acquired by the pacemaker and transmitted to the APM server, the selection processor circuitry evaluates the efficacy of a capture verification mode selects a capture verification mode based on the efficacy evaluation. The APM system communicates the selection to the pacemaker and the pacemaker may modify the capture verification mode used for pacing based on the selection.

In yet another implementation, data associated with capture verification mode efficacy may be downloaded from a pacemaker 420 and stored at an APM patient information server 440. The physician and/or the patient may communicate with the patient information server 440, for example, to the view or otherwise acquire the data associated with capture verification mode efficacy. The physician or other person may select a capture verification mode based on the capture verification mode efficacy data. The selection is communicated to the pacemaker 420 for implementation via a wireless communication channel The patient-internal medical device 420 may be a fully or partially implantable device that performs monitoring, diagnosis, and/or therapy functions. The patient-external medical device 430 may perform monitoring, diagnosis and/or therapy functions external to the patient (i.e., not invasively implanted within the patient's body). The patient-external medical device 430 may be positioned on the patient, near the patient, or in any location external to the patient. It is understood that a portion of a patient-external medical device 430 may be positioned within an orifice of the body, such as the nasal cavity or mouth, yet can be considered external to the patient (e.g., mouth pieces/appliances, tubes/appliances for nostrils, or temperature sensors positioned in the ear canal).

The patient-internal and patient-external medical devices 420, 430 may be coupled to one or more sensors 421, 422, 431, 432, patient input devices 424, 434 and/or other information acquisition devices 426, 436. The sensors 421, 422, 431, 432, patient input devices 424, 434, and/or other information acquisition devices 426, 436 may be employed to detect conditions relevant to the monitoring, diagnostic, and/or therapeutic functions of the patient-internal and patient-external medical devices 420, 430.

The medical devices 420, 430 may each be coupled to one or more patient-internal sensors 421, 431 that are fully or partially implantable within the patient. The medical devices 420, 430 may also be coupled to patient-external sensors 422, 432 positioned on the patient, near the patient, or in a remote location with respect to the patient. The patient-internal 421, 431 and patient-external 422, 432 sensors may be used to sense conditions, such as physiological or environmental conditions, that affect the patient.

The patient-internal sensors 421 may be coupled to the patient-internal medical device 420 through implanted leads. In one example, an internal endocardial lead system is used to couple sensing electrodes to an implantable pacemaker or other cardiac rhythm management device. One or more of the patient-internal sensors 421, 431 may be equipped with transceiver circuitry to support wireless communication between the one or more patient-internal sensors 421, 431 and the patient-internal medical device 420 and/or the patient-external medical device 430.

The patient-external sensors 422, 432 may be coupled to the patient-internal medical device 420 and/or the patient-external medical device 430 through leads or through wireless connections. Patient-external sensors 422 preferably communicate with the patient-internal medical device 420 wirelessly. Patient-external sensors 432 may be coupled to the patient-external medical device 430 through leads or through a wireless link.

The medical devices 420, 430 may be coupled to one or more patient-input devices 424, 434. The patient-input devices 424, 434 facilitate manual transfer of information to the medical devices 420, 430 by the patient. The patient input devices 424, 434 may be particularly useful for inputting information concerning patient perceptions or patient-known factors, such as patient smoking, drug use, or other factors that are not automatically sensed or detected by the medical devices 420, 430. In one implementation, a device programmer may be used to facilitate patient input to a medical device 420, 430.

The medical devices 420, 430 may be connected to one or more information systems 426, 436, for example, a database that stores information useful in connection with the monitoring, diagnostic, or therapy functions of the medical devices 420, 430.

In one embodiment, the patient-internal medical device 420 and the patient-external medical device 430 may communicate through a wireless link between the medical devices 420, 430. For example, the patient-internal and patient-external devices 420, 430 may be coupled through a short-range radio link, such as Bluetooth or a wireless link. The communications link may facilitate uni-directional or bi-directional communication between the patient-internal 420 and patient-external 430 medical devices. Data and/or control signals may be transmitted between the patient-internal 420 and patient-external 430 medical devices to coordinate the functions of the medical devices 420, 430.

The patient-internal medical device 420 and/or the patient-external medical device 430 may be coupled through a wireless or wired communications link to a patient information server that is part of an advanced patient management (APM) system 440. The APM patient information server 440 may be used to download and store data collected by the patient-internal and patient-external medical devices 420, 430.

The data stored on the APM patient information server 440 may be accessible by the patient and the patient's physician through terminals 450, e.g., remote computers located in the patient's home or the physician's office. The APM patient information server 440 may be used to communicate to one or more of the patient-internal and patient-external medical devices 420, 430 to effect remote control of the monitoring, diagnosis, and/or therapy functions of the medical devices 420, 430. For example, after the physician selects a capture verification mode, then the APM system may communicate the selection to the appropriate medical device to effect the change in capture verification mode.

In one scenario, the patient-internal and patient-external medical devices 420, 430 may not communicate directly with each other, but may communicate indirectly through the APM system 440. In this embodiment, the APM system 440 may operate as an intermediary between two or more of the medical devices 420, 430. For example, data and/or control information may be transferred from one of the medical devices 420, 430 to the APM system 440. The APM system 440 may transfer the data and/or control information to another of the medical devices 420, 430.

Although the present system is described in conjunction with an implantable cardiac defibrillator having a microprocessor-based architecture, it will be understood that the implantable cardiac defibrillator (or other device) may be implemented in any logic-based integrated circuit architecture, if desired.

Figure 5:
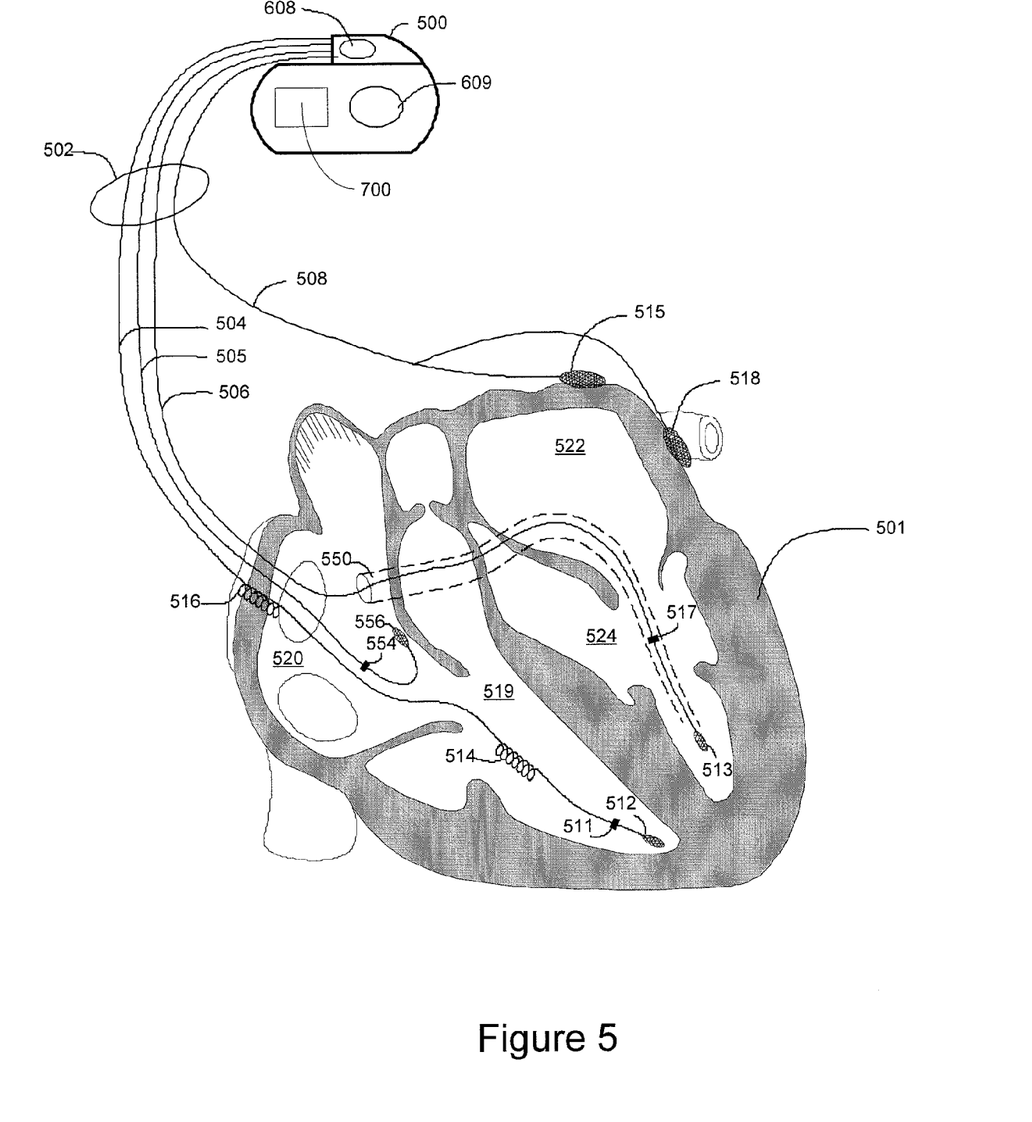
FIG. 5 is a partial view of one embodiment of an implantable medical device in accordance with embodiments of the invention.

Referring now to FIG. 5 of the drawings, there is shown a cardiac rhythm management (CRM) device that may be used to implement capture verification methods of the present invention. The CRM device 500 is electrically and physically coupled to a lead system 502. Capture verification circuitry 700, such as the capture verification circuitry described in connection with FIG. 7, and elsewhere herein, may be disposed within the housing of the CRM device 500. The housing and/or header of the CRM device 500 may incorporate one or more electrodes 608, 609 used to provide electrical stimulation energy to the heart and to sense cardiac electrical activity. The CRM device 500 may utilize all or a portion of the CRM system housing as a can electrode 609. The CRM device 500 may include an indifferent electrode positioned, for example, on the header or the housing of the CRM device 500. If the CRM device 500 includes both a can electrode 609 and an indifferent electrode 608, the electrodes 608, 609 typically are electrically isolated from each other.

The lead system 502 is used to detect electric cardiac signals produced by the heart 501 and to provide electrical energy to the heart 501 under certain predetermined conditions to treat cardiac arrhythmias. The lead system 502 may include one or more electrodes used for pacing, sensing, and/or defibrillation. In the embodiment shown in FIG. 5, the lead system 502 includes an intracardiac right ventricular (RV) lead system 504, an intracardiac right atrial (RA) lead system 505, an intracardiac left ventricular (LV) lead system 506, and an extracardiac left atrial (LA) lead system 508. The lead system 502 of FIG. 5 illustrates one embodiment that may be used in connection with the cardiac response classification methodologies described herein. Other leads and/or electrodes may additionally or alternatively be used.

The lead system 502 may include intracardiac leads 504, 505, 506 implanted in a human body with portions of the intracardiac leads 504, 505, 506 inserted into a heart 501. The intracardiac leads 504, 505, 506 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 5, the lead system 502 may include one or more extracardiac leads 508 having electrodes, e.g., epicardial electrodes, positioned at locations outside the heart for sensing and pacing one or more heart chambers.

The right ventricular lead system 504 illustrated in FIG. 5 includes an SVC-coil 516, an RV-coil 514, an RV-ring electrode 511, and an RV-tip electrode 512. The right ventricular lead system 504 extends through the right atrium 520 and into the right ventricle 519. In particular, the RV-tip electrode 512, RV-ring electrode 511, and RV-coil electrode 514 are positioned at appropriate locations within the right ventricle 519 for sensing and delivering electrical stimulation pulses to the heart. The SVC-coil 516 is positioned at an appropriate location within the right atrium chamber 520 of the heart 501 or a major vein leading to the right atrial chamber 520 of the heart 501.

In one configuration, the RV-tip electrode 512 referenced to the can electrode 609 may be used to implement unipolar pacing and/or sensing in the right ventricle 519. Bipolar pacing and/or sensing in the right ventricle may be implemented using the RV-tip 512 and RV-ring 511 electrodes. In yet another configuration, the RV-ring 511 electrode may optionally be omitted, and bipolar pacing and/or sensing may be accomplished using the RV-tip electrode 512 and the RV-coil 514, for example. The right ventricular lead system 504 may be configured as an integrated bipolar pace/shock lead. The RV-coil 514 and the SVC-coil 516 are defibrillation electrodes.

The left ventricular lead 506 includes an LV distal electrode 513 and an LV proximal electrode 517 located at appropriate locations in or about the left ventricle 524 for pacing and/or sensing the left ventricle 524. The left ventricular lead 506 may be guided into the right atrium 520 of the heart via the superior vena cava. From the right atrium 520, the left ventricular lead 506 may be deployed into the coronary sinus ostium, the opening of the coronary sinus 550. The lead 506 may be guided through the coronary sinus 550 to a coronary vein of the left ventricle 524. This vein is used as an access pathway for leads to reach the surfaces of the left ventricle 524 which are not directly accessible from the right side of the heart. Lead placement for the left ventricular lead 506 may be achieved via subclavian vein access and a preformed guiding catheter for insertion of the LV electrodes 513, 517 adjacent to the left ventricle.

Unipolar pacing and/or sensing in the left ventricle may be implemented, for example, using the LV distal electrode referenced to the can electrode 609. The LV distal electrode 513 and the LV proximal electrode 517 may be used together as bipolar sense and/or pace electrodes for the left ventricle. The left ventricular lead 506 and the right ventricular lead 504, in conjunction with the CRM device 500, may be used to provide cardiac resynchronization therapy such that the ventricles of the heart are paced substantially simultaneously, or in phased sequence, to provide enhanced cardiac pumping efficiency for patients suffering from chronic heart failure.

The right atrial lead 505 includes a RA-tip electrode 556 and an RA-ring electrode 554 positioned at appropriate locations in the right atrium 520 for sensing and pacing the right atrium 520. In one configuration, the RA-tip 556 referenced to the can electrode 609, for example, may be used to provide unipolar pacing and/or sensing in the right atrium 520. In another configuration, the RA-tip electrode 556 and the RA-ring electrode 554 may be used to effect bipolar pacing and/or sensing.

FIG. 5 illustrates one embodiment of a left atrial lead system 508. In this example, the left atrial lead 508 is implemented as an extracardiac lead with LA distal 518 and LA proximal 515 electrodes positioned at appropriate locations outside the heart 501 for sensing and pacing the left atrium 522. Unipolar pacing and/or sensing of the left atrium may be accomplished, for example, using the LA distal electrode 518 to the can 609 pacing vector. The LA proximal 515 and LA distal 518 electrodes may be used together to implement bipolar pacing and/or sensing of the left atrium 522.

Figure 6:
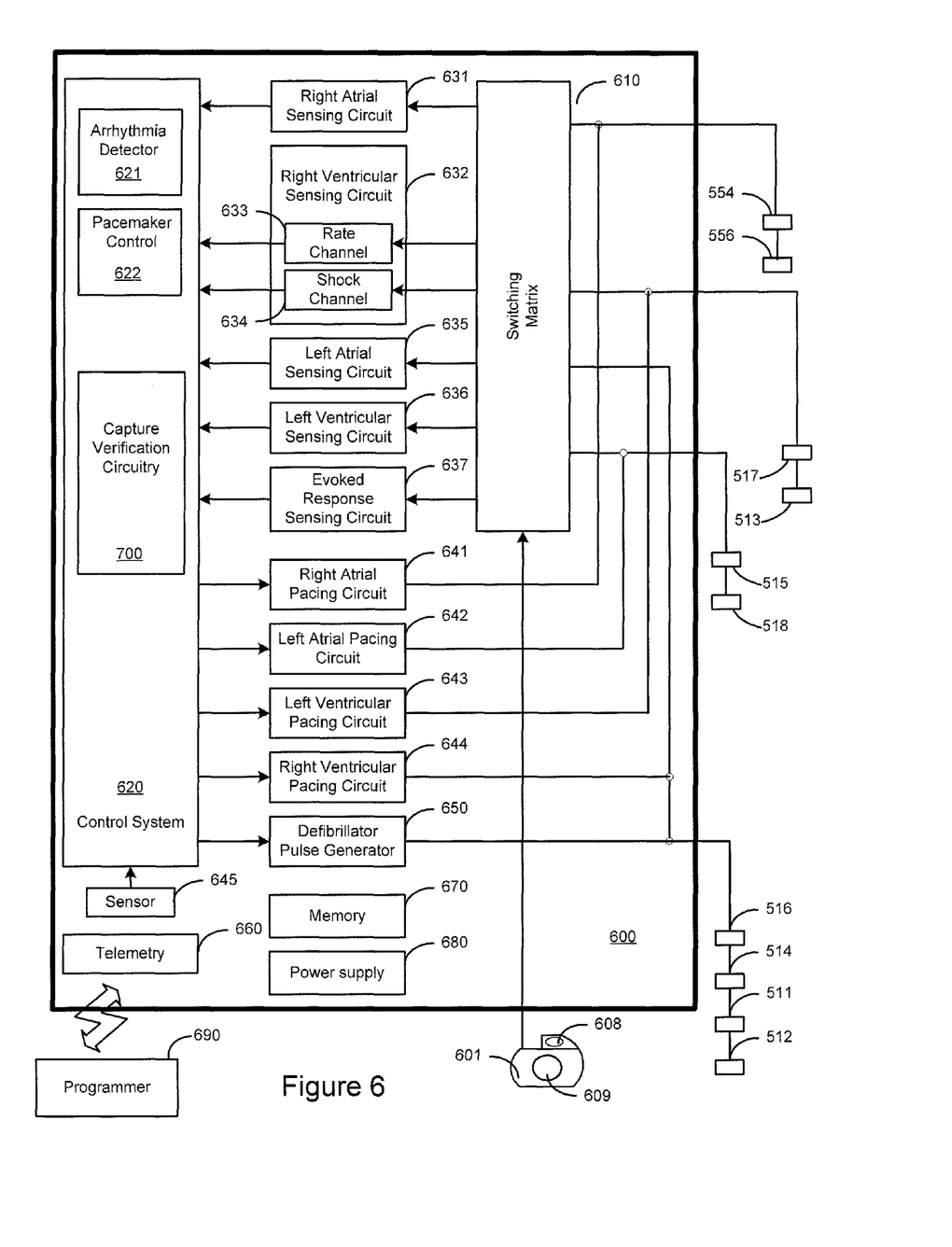
FIG. 6 is a block diagram of an implantable medical device that may be used to verify capture using automatic capture verification modes in accordance with embodiments of the invention.

Referring now to FIG. 6, there is shown an embodiment of a cardiac rhythm management (CRM) system 600 suitable for implementing a capture verification methodology of the present invention. FIG. 6 shows a CRM system 600 divided into functional blocks. It is understood by those skilled in the art that there exist many possible configurations in which these functional blocks can be arranged. The example depicted in FIG. 6 is one possible functional arrangement. Other arrangements are also possible. For example, more, fewer or different functional blocks may be used to describe a cardiac defibrillator suitable for implementing the methodologies for verifying capture using a number of capture verification modes in accordance with methods of the present invention. In addition, although the CRM system 600 depicted in FIG. 6 contemplates the use of a programmable microprocessor-based logic circuit, other circuit implementations may be utilized.

The CRM system 600 depicted in FIG. 6 includes circuitry for receiving cardiac signals from a heart and delivering electrical stimulation energy to the heart in the form of pacing pulses or defibrillation shocks. In one embodiment, the circuitry of the CRM system 600 is encased and hermetically sealed in a housing 601 suitable for implanting in a human body. Power to the CRM system 600 is supplied by an electrochemical battery 680. A connector block (not shown) is attached to the housing 601 of the CRM system 600 to allow for the physical and electrical attachment of the lead system conductors to the circuitry of the CRM system 600.

The CRM system 600 may be a programmable microprocessor-based system, including a control system 620 and a memory 670. The memory 670 may store information associated with capture verification mode selection, along with other information. The memory 670 may be used, for example, for storing historical EGM and therapy data. The historical data storage may include data obtained from long term patient monitoring used for trending or other diagnostic purposes. Historical data, as well as other information, may be transmitted to an external programmer unit 690 as needed or desired.

The control system 620 and memory 670 may cooperate with other components of the CRM system 600 to control the operations of the CRM system 600. The control system depicted in FIG. 6 incorporates a capture verification circuitry 700 for evaluating an efficacy of capture verification modes and selecting from a variety of capture verification modes or a high output fixed voltage mode in accordance with various embodiments of the present invention. The control system 620 may include additional functional components including a pacemaker control circuit 622, an arrhythmia detector 621, and a template processor for cardiac signal morphology analysis, along with other components for controlling the operations of the CRM system 600.

Telemetry circuitry 660 may be implemented to provide communications between the CRM system 600 and an external programmer unit 690. In one embodiment, the telemetry circuitry 660 and the programmer unit 690 communicate using a wire loop antenna and a radio frequency telemetric link, as is known in the art, to receive and transmit signals and data between the programmer unit 690 and the telemetry circuitry 660. In this manner, programming commands and other information may be transferred to the control system 620 of the CRM system 600 from the programmer unit 690 during and after implant. In addition, stored cardiac data pertaining to capture threshold, capture detection and/or cardiac response classification, for example, along with other data, may be transferred to the programmer unit 690 from the CRM system 600.

In the embodiment of the CRM system 600 illustrated in FIG. 6, electrodes RA-tip 556, RA-ring 554, RV-tip 512, RV-ring 511, RV-coil 514, SVC-coil 516, LV distal electrode 513, LV proximal electrode 517, LA distal electrode 518, LA proximal electrode 515, indifferent electrode 608, and can electrode 609 are coupled through a switch matrix 610 to sensing circuits 631-637.

A right atrial sensing circuit 631 serves to detect and amplify electrical signals from the right atrium of the heart. Bipolar sensing in the right atrium may be implemented, for example, by sensing voltages developed between the RA-tip 556 and the RA-ring 554. Unipolar sensing may be implemented, for example, by sensing voltages developed between the RA-tip 556 and the can electrode 609. Outputs from the right atrial sensing circuit are coupled to the control system 620.

A right ventricular sensing circuit 632 serves to detect and amplify electrical signals from the right ventricle of the heart. The right ventricular sensing circuit 632 may include, for example, a right ventricular rate channel 633 and a right ventricular shock channel 634. Right ventricular cardiac signals sensed through use of the RV-tip 512 electrode are right ventricular near-field signals and are denoted RV rate channel signals. A bipolar RV rate channel signal may be sensed as a voltage developed between the RV-tip 512 and the RV-ring 511. Alternatively, bipolar sensing in the right ventricle may be implemented using the RV-tip electrode 512 and the RV-coil 514. Unipolar rate channel sensing in the right ventricle may be implemented, for example, by sensing voltages developed between the RV-tip 512 and the can electrode 609.

Right ventricular cardiac signals sensed through use of the RV-coil electrode 514 are far-field signals, also referred to as RV morphology or RV shock channel signals. More particularly, a right ventricular shock channel signal may be detected as a voltage developed between the RV-coil 514 and the SVC-coil 516. A right ventricular shock channel signal may also be detected as a voltage developed between the RV-coil 514 and the can electrode 609. In another configuration the can electrode 609 and the SVC-coil electrode 516 may be electrically shorted and a RV shock channel signal may be detected as the voltage developed between the RV-coil 514 and the can electrode 609/SVC-coil 516 combination.

Outputs from the right ventricular sensing circuit 632 are coupled to the control system 620. In one embodiment of the invention, rate channel signals and shock channel signals may be used to develop morphology templates for analyzing cardiac signals. In this embodiment, rate channel signals and shock channel signals may be transferred from the right ventricular sensing circuit 632 to the control system 620 and to a template processor where the morphological characteristics of a cardiac signal are analyzed for arrhythmia detection.

Left atrial cardiac signals may be sensed through the use of one or more left atrial electrodes 515, 518, which may be configured as epicardial electrodes. A left atrial sensing circuit 635 serves to detect and amplify electrical signals from the left atrium of the heart. Bipolar sensing and/or pacing in the left atrium may be implemented, for example, using the LA distal electrode 518 and the LA proximal electrode 515. Unipolar sensing and/or pacing of the left atrium may be accomplished, for example, using the LA distal electrode 518 to can vector 609 or the LA proximal electrode 515 to can vector 609.

A left ventricular sensing circuit 636 serves to detect and amplify electrical signals from the left ventricle of the heart. Bipolar sensing in the left ventricle may be implemented, for example, by sensing voltages developed between the LV distal electrode 513 and the LV proximal electrode 517. Unipolar sensing may be implemented, for example, by sensing voltages developed between the LV distal electrode 513 or the LV proximal electrode 517 to the can electrode 609.

Optionally, an LV coil electrode (not shown) may be inserted into the patient's cardiac vasculature, e.g., the coronary sinus, adjacent the left heart. Signals detected using combinations of the LV electrodes, 513, 517, LV coil electrode (not shown), and/or can electrodes 609 may be sensed and amplified by the left ventricular sensing circuitry 636. The output of the left ventricular sensing circuit 636 is coupled to the control system 620.

The outputs of the switching matrix 610 may be operated to couple selected combinations of electrodes 511, 512, 513, 514, 515, 516, 517, 518, 556, 554 to various sensing circuits 631-636. An evoked response sensing circuit 637 may be used to sense and amplify voltages developed using various combinations of electrodes. An evoked response sensing circuit 637 may be used to sense cardiac signals indicative of a cardiac response to pacing, e.g., capture or non-capture. Cardiac signals indicative of the cardiac pacing response are sensed and amplified by the evoked response circuit 637 and are analyzed by a capture detector to determine cardiac pacing response.

The CRM system 600 may incorporate one or more metabolic sensors 645 for sensing the activity and/or hemodynamic need of the patient. Rate-adaptive pacemakers typically utilize metabolic sensors to adapt the pacing rate to match the patient's hemodynamic need. A rate-adaptive pacing system may use an activity or respiration sensor to determine an appropriate pacing rate. Patient activity may be sensed, for example, using an accelerometer disposed within the housing of the pulse generator. Transthoracic impedance, which may be measured, for example, via the intracardiac electrodes, may be used to determine respiration rate. Sensor information from the metabolic sensor is used to adjust the pacing rate to support the patient's hemodynamic need.

Figure 7:
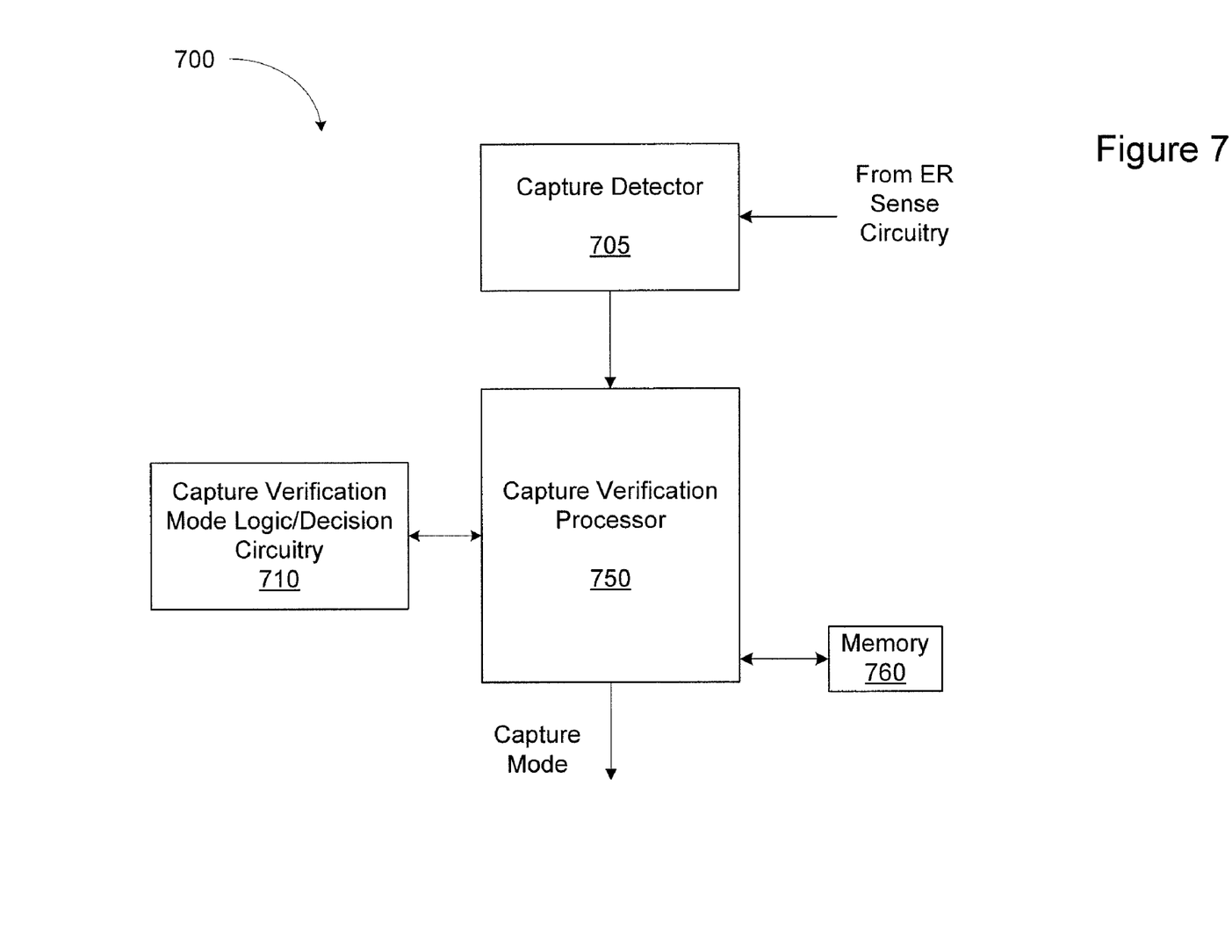
FIG. 7 is a block diagram of capture verification mode selection circuitry in accordance with embodiments of the invention.

FIG. 7 illustrates a block diagram of capture verification circuitry 700 that may be utilized to implement capture verification mode selection in accordance with embodiments of the invention. The capture verification circuitry 700 includes a capture detector 705 that receives signals from an ER sensing circuit. Based on the characteristics of the signals sensed by the ER sensing circuit, the capture detector 705 determines the cardiac response to pacing. The capture detector 705 communicates with other components of the capture verification circuitry 700, including capture verification mode logic/decision circuitry 710, and the capture verification processor 750 to provide capture detection acquired during implementation of ACD mode or CTT mode.

As previously discussed, the pacing may be provided to the patient with capture verification implemented via a plurality of modes, including at least ACD mode and CTT mode. Capture verification mode logic/decision circuitry 710 includes circuitry for selecting between ACD mode and CTT mode, and implementing ACD mode beat by beat automatic capture verification, implementing CTT mode periodic threshold searching without intervening beat by beat capture detection, or implementing a fixed voltage mode or a trend only mode, for example.

Information associated with the efficacy of the ACD mode or the CTT mode may be evaluated by the capture verification processor 750. Prior to the evaluation, the information may be stored in memory 760 for later access by the capture verification processor 750. The capture verification processor 750 may select an appropriate or desirable capture verification mode based on the efficacy evaluation. If the efficacy evaluation indicates that neither the ACD mode nor the CTT mode is desirable, the capture verification processor 750 may initiate fixed voltage pacing implemented using capture verification mode logic/decision circuitry 710, or may initiate a fixed voltage pacing ACD mode circuitry using capture verification mode logic/decision circuitry 710, for example.

Various modifications and additions may be made to the embodiments discussed herein without departing from the scope of the present invention. Accordingly, the scope of the present invention should not be limited by the particular embodiments described above, but should be defined only by the claims set forth below and equivalents thereof.

What is claimed is:

1. A cardiac rhythm management system, comprising:
 a plurality of cardiac electrodes;
 a pulse generator coupled to the electrodes, the pulse generator configured to deliver pacing pulses to the heart;
 circuitry configured to implement a plurality of capture verification modes, including:
 an automatic capture detection (ACD) mode comprising beat by beat capture verification wherein a backup pace is delivered by the pulse generator if capture is not detected for a delivered pace pulse; and
 a capture threshold testing (CTT) mode comprising threshold testing according to a schedule without intervening beat by beat capture detection; and
 a processor configured to evaluate one or more of frequency of backup pace delivery of the ACD mode and frequency of threshold searches, the processor configured to select one of the plurality of capture verification modes based on at least one of frequency of backup pacing and frequency of threshold searches.

2. The system of claim 1, wherein the processor is configured to evaluate the frequency of threshold searches by comparing the frequency of threshold searches to a threshold value and to select the CCT mode if the frequency of threshold searches exceeds the threshold value.

3. The system of claim 1, wherein the processor is configured to evaluate the frequency of backup pace delivery by comparing the frequency of backup pace delivery to a threshold value and to select the CCT mode if the frequency of backup pace delivery exceeds the threshold value.

4. The system of claim 1, wherein the processor is configured to one or more of frequency of backup pace delivery of the ACD mode and frequency of threshold searches by an event.

5. The system of claim 4, wherein the event comprises one or more of performance of a threshold search and delivery of a backup pace.

6. A method of operating a cardiac rhythm management system capable of operating in a plurality of capture verification modes including an automatic beat by beat capture detection (ACD) mode and in a capture threshold testing (CTT) mode in which capture threshold searches are performed without intervening beat by beat capture detection between successive capture threshold searches, the method comprising:
  evaluating one or more of frequency of backup pace delivery of the ACD mode, frequency of triggered threshold searches of the ACD mode, time spent in a CCT retry state, time spent in a fixed energy pacing mode, and energy consumption of at least one of the capture verification modes; and
  selecting one of the plurality of capture verification modes based on at least one of the frequency of backup pace delivery of the ACD mode, the frequency of triggered threshold searches of the ACD mode, the time spent in a CCT retry state, the time spent in a fixed pacing mode, and the energy consumption of at least one of the capture verification modes.

7. The method of claim 6, wherein:
  evaluating comprises evaluating the frequency of backup pace delivery of the ACD mode; and
  selecting comprises selecting one of the plurality of capture verification modes comprises selecting based on the frequency of backup pace delivery of the ACD mode.

8. The method of claim 6, wherein:
  evaluating comprises evaluating the frequency of triggered threshold searches of the ACD mode; and
  selecting comprises selecting one of the plurality of capture verification modes comprises selecting based on the frequency of triggered threshold searches of the ACD mode.

9. The method of claim 6, wherein:
  evaluating comprises evaluating the time spent in a CCT retry state; and
  selecting comprises selecting one of the plurality of capture verification modes comprises selecting based on the time spent in a CCT retry state.

10. The method of claim 6, wherein:
  evaluating comprises evaluating the time spent in a fixed energy pacing mode; and
  selecting comprises selecting one of the plurality of capture verification modes comprises selecting based on the time spent in a fixed energy pacing mode.

11. The method of claim 6, wherein:
  evaluating comprises evaluating the energy consumption of at least one of the capture verification modes; and
  selecting comprises selecting one of the plurality of capture verification modes comprises selecting based on the energy consumption of at least one of the capture verification modes.

12. The method of claim 6, wherein evaluating further comprises evaluating based on an absence of fusion beats detected during threshold searches.

13. The method of claim 6, wherein evaluating further comprises evaluating based on compatibility with reverse mode switch algorithms.

14. The method of claim 6, wherein evaluating further comprises evaluating based on compatibility with atrioventricular (AV) delay programming.

15. The method of claim 6, wherein evaluating further comprises evaluating based on history of atrial tachyarrhythmia mode switch response.

16. The method of claim 6, wherein evaluating further comprises evaluating based on low percentage of ventricular paces.

* * * * *